(12) United States Patent
Aramata et al.

(10) Patent No.: US 6,984,748 B2
(45) Date of Patent: Jan. 10, 2006

(54) CO-CATALYST AND PROCESS FOR THE PREPARATION OF ORGANOHALOSILANES

(75) Inventors: Mikio Aramata, Annaka (JP); Hideaki Ozeki, Annaka (JP); Akio Muraida, Annaka (JP); Susumu Ueno, Annaka (JP); Toshio Shinohara, Annaka (JP); Tetsuya Inukai, Annaka (JP)

(73) Assignee: Shin-Etsu Chemical Co., LTD, Tokyo (JP)

( * ) Notice: Subject to any disclaimer, the term of this patent is extended or adjusted under 35 U.S.C. 154(b) by 0 days.

(21) Appl. No.: 10/119,146

(22) Filed: Apr. 10, 2002

(65) Prior Publication Data
US 2002/0183536 A1 Dec. 5, 2002

(30) Foreign Application Priority Data
Apr. 10, 2001 (JP) .............................. 2001-110805

(51) Int. Cl.
*C07F 7/16* (2006.01)
(52) U.S. Cl. .................. 556/472; 556/400; 556/465
(58) Field of Classification Search ................ 502/344, 502/345; 556/400, 465, 472
See application file for complete search history.

(56) References Cited

U.S. PATENT DOCUMENTS

| 4,504,597 A | 3/1985 | Klar et al. |
| 4,520,130 A | 5/1985 | Hashiguchi et al. |
| 5,817,855 A * | 10/1998 | Langner et al. ............. 556/472 |
| 6,288,258 B1 * | 9/2001 | Aramata et al. ............. 556/472 |
| 6,365,766 B1 * | 4/2002 | Aramata et al. ............. 556/472 |
| 6,395,917 B1 * | 5/2002 | Ishizaka et al. ............. 556/472 |
| 6,686,312 B1 * | 2/2004 | Aramata et al. ............. 502/345 |

FOREIGN PATENT DOCUMENTS

| JP | 9-173844 | 7/1997 |
| JP | 2000-254506 | 9/2000 |

OTHER PUBLICATIONS

CA:108:150711 abs of CN 85102880 Sep. 1986.*
CA:91:78090 abs of JP54002901.*
Ralph E. Ricksecker, "Copper alloys", in AccessScience@McGraw-Hill, http://www.accessscience.com, DOI 10.1036/1097-8542. 161000, Apr. 10, 2000, pp. 1-6.*

* cited by examiner

*Primary Examiner*—Rosalynd Keys
(74) *Attorney, Agent, or Firm*—Birch, Stewart, Kolasch & Birch, LLP

(57) ABSTRACT

In a Rochow process, organohalosilanes are prepared by reacting metallic silicon particles with an organohalide in the presence of a copper catalyst and a co-catalyst. The invention uses as the co-catalyst a powder of co-catalyst active element-copper alloy containing substantial strain energy because this co-catalyst can reduce the activation time taken until a steady state is reached, which has been an outstanding problem in Rochow reaction, maintain the steady state over time and increase the selectivity of desired diorganodihalosilane for eventually increasing the yield based on the starting silicon.

6 Claims, 5 Drawing Sheets

CO-CATALYST AND PROCESS FOR THE PREPARATION OF ORGANOHALOSILANES

This invention generally relates to a process for preparing organohalosilanes by reacting metallic silicon particles with an organohalide by Rochow method and more particularly, to a co-catalyst used in the process.

BACKGROUND OF THE INVENTION

Synthesis of organohalosilanes such as methylchlorosilane is industrially carried out by directly reacting organic halides such as alkyl halides or phenyl halides with metallic silicon particles in the presence of a copper catalyst at a temperature of 250 to 500° C., which is known as Rochow reaction. For this reaction, it is a key technology to produce the desired organohalosilane in high yields while keeping a high reaction rate. For example, in the case of methylchlorosilane synthesis, it is a key to increase the selectivity of dimethyldichlorosilane in the most demand, and in the case of phenylsilane synthesis, it is a key to produce desired diphenyldichlorosilane and phenyltrichlorosilane in a composition conforming to their demand. However, this reaction takes a long time for activation until a steady state is reached, and in turn, the steady state is relatively short so that the contact mass declines its activity with the passage of time, leading to a rapid drop of the yield of diorganodichlorosilane. For example, the synthesis of methylsilane often entails side reactions to increase a high-boiling fraction such as disilanes, methyltrichlorosilane and other unwanted products, which requires premature replacement of the contact mass within the reactor and removal of scale. It is known that these problems can be solved by effecting reaction in the presence of various co-catalysts such as zinc, tin and phosphorus. With respect to the co-catalysts, while too much emphasis is made on their positive functions, little study has been made on their negative functions. The current practice is merely to change, on an empirical basis, the composition of additional contact mass with the progress of reaction.

Making a close study on the action mechanism of the co-catalyst used in Rochow reaction and the behavior thereof within a reactor, the inventor attempted to optimize the form of the co-catalyst. An object of the invention is to provide a co-catalyst for use in organohalosilane synthesis which can reduce the activation time taken until a steady state is reached, which has been an outstanding problem in Rochow reaction, and increase the selectivity of desired diorganodihalosilane for eventually improving the reaction results. Another object of the invention is to provide a process for preparing organohalosilanes using the co-catalyst.

SUMMARY OF THE INVENTION

Making a close study on the behavior and action mechanism of co-catalysts, the inventor found that the co-catalysts have substantial negative functions as well as positive functions. The inventor has reached the conclusion that in order to achieve satisfactory reaction results while minimizing the negative functions, the co-catalyst to be added must become rapidly effective in every step during the reaction. More particularly, Rochow reaction is industrially carried out in reactors such as fluidized bed, vibratory fluidized bed and agitation fluidized bed reactors wherein a metallic silicon powder and a copper catalyst as main starting materials having added thereto a co-catalyst of zinc, tin, antimony, phosphorus or aluminum in metal, oxide or alloy form, are sequentially added to the reaction system to form the contact mass. Since this reaction is a very complex reaction between a solid and a liquid, it is very important for the management of reaction to effect the reaction while reducing the activation time (time required for activation until reaction reaches a steady state), minimizing any drop of activity due to deposition of deactivated contact mass with the progress of reaction, that is, drops of reaction rate and selectivity, and minimizing any increase of reactor residues (high-boiling fraction such as disilanes) which are unwanted products. In the current practice, various co-catalysts are used in order to control these factors. Many such co-catalysts have not only positive functions of promoting the reaction, but also negative functions. It is then very important for these co-catalysts to effectively work in every step of the reaction process. That is, it is important that the co-catalysts be added in a rapid acting form.

Now the positive and negative aspects of the behavior of typical co-catalysts are described. Zinc acts in the form of zinc chloride which propagates through a gas phase. It contributes to the increased selectivity of diorganodihalosilane during principal reaction by controlling side reaction, but due to its relatively low vapor pressure, zinc chloride condenses and accumulates in a cooled portion within the reactor, leading to a decrease of heat conductivity. This impedes removal of reaction heat, eventually leading to a decrease of reaction time, with the results of reaction being exacerbated. Aluminum (most often, aluminum contained as an impurity in one reactant, metallic silicon is utilized) acts in the form of aluminum chloride ($AlCl_3$) and performs a very important function in imparting initial activity to the contact mass, that is, at the onset of reaction. However, since aluminum chloride is a strong Lewis acid, it can act as a disproportionation reaction catalyst for the diorganodihalosilane formed and as a result, invite a drop of the selectivity of diorganodihalosilane. Tin also acts in the form of tin chloride. Although the amount of tin added to the contact mass is very small as compared with zinc, tin is very effective for increasing the reaction rate and the selectivity of diorganodihalosilane. If tin is added in excessive amounts, there is formed a more proportion of a high-boiling fraction such as disilanes which are essentially unwanted products in the current supply/demand balance of organohalosilanes. As seen from the above discussion, the co-catalyst required differs depending on the reaction state, and every co-catalyst has both advantages and disadvantages. Understandably, it is important for the co-catalyst to work immediately when necessary or when added, that is, rapid action. Since these co-catalysts are generally added in small or trace amounts relative to the contact mass (and the copper catalyst too), it is preferred that the co-catalyst be added in the form of a compound, mixture or alloy with copper and readily converted to the workable state, that is, halide (typically chloride).

Making studies from the foregoing standpoint on the form of various co-catalyst elements and the reactivity thereof with organic halides such as methyl chloride, the inventor has learned the following. Copper is fully ductile, and copper alloys with zinc, known as brass, are ductile over a wide range of mixing ratio. Even when another element is added to copper and brass, if in a small amount, sufficient ductility is maintained. It is then preferred that the co-catalyst element be present in the form of a copper alloy which can be given strain by mechanical working such as rolling and stamping. The activity of the co-catalyst element-copper alloy largely depends on the magnitude of strain energy the copper alloy possesses. A large amount of strain energy and a large surface area are essential for the copper alloy to develop high activity. In the reaction, the co-catalyst is admitted into the reactor as the contact mass which is a mixture thereof with the copper catalyst and metallic silicon powder and supplemented with the progress of reaction to form organochlorosilane. Since the action or composition of the co-catalyst required differs with the reaction state, the co-catalyst is desired to be capable of rapid action, that is, to exert its effect to a full extent immediately after supplement. The inventor has come to the conclusion that the preferred form of the co-catalyst that can accomplish this end is a copper alloy containing substantial strain energy.

For the reaction of this type, it is known to use the co-catalyst in the form of a copper alloy. The importance of crystal lattice strain in metallic copper catalysts is disclosed in JP-A 2000-254506 together with its evaluation method. In the event where copper oxide is used as the catalyst, the importance of the strain energy in copper oxide powder is already known as disclosed in JP-A 9-173844, U.S. Pat. Nos. 4,520,130 and 4,504,597. However, a co-catalyst taking advantage of working strain and its evaluation method have not been developed.

Therefore, the present invention provides a co-catalyst having high and consistent activity and capable of rapid action in the synthesis of organohalosilanes and a process for preparing organohalosilanes using the co-catalyst, thereby overcoming the outstanding problems.

In connection with a process for preparing organohalosilanes by reacting metallic silicon particles with an organohalide in the presence of a copper catalyst and a co-catalyst, the invention provides the co-catalyst comprising a copper alloy powder of a co-catalyst active element alloyed with copper containing substantial strain energy.

In a preferred embodiment, the copper alloy powder is a copper alloy foil powder, stamped copper alloy powder or microscopic copper alloy powder. The copper alloy is most often an alloy of copper with at least one element selected from the group consisting of zinc, tin, antimony, phosphorus and aluminum. In another preferred embodiment, the co-catalyst possesses the crystal lattice strain energy which relaxes at a temperature of up to 400° C., and has a specific surface area of 0.05 to 2.0 m²/g as measured by the BET or air-permeability method. The co-catalyst, when heated in air, may undergo rapid surface oxidation concomitant with the relaxation of the strain energy. Preferably, the co-catalyst, on air flow differential thermal analysis, exhibits an incipient heat generation temperature of up to 400° C. with an exothermic value of 1 to 80 cal/g.

In another aspect, the invention provides a process for preparing organohalosilanes by reacting metallic silicon particles with an organohalide in the presence of a copper catalyst and the co-catalyst defined above.

DESCRIPTION OF THE PREFERRED EMBODIMENTS

Figure 1A:
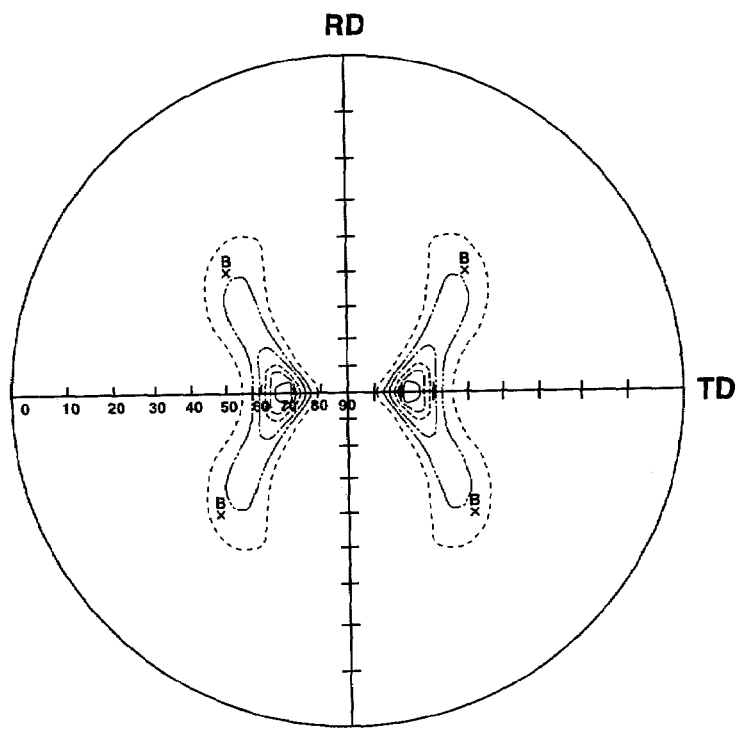
FIG. 1 is a x-ray diffraction pattern of rolled copper, which is a pole figure of [200] axis (B direction) relative to (100) plane, FIG. 1A being rolled copper and FIG. 1B being rolled copper after annealing at 300° C.

The present invention pertains to Rochow reaction, that is, the synthesis of organohalosilanes of the general formula:

$$R_n SiX_{4-n}$$

wherein R is $C_{1-4}$ alkyl or aryl, X is halogen, and n is an integer of 1–3, by reacting a metallic silicon powder with a gas or vapor of an organic halide such as alkyl halide or aryl halide in the presence of a copper catalyst and a co-catalyst such as zinc, tin, antimony, aluminum or phosphorus. Specifically, the invention relates to the co-catalyst used in this reaction. While prior art co-catalysts lack rapid-acting nature, which has precluded the effective progress of reaction, the invention intends to offer an active co-catalyst which can effectively exert the co-catalytic effects required in various reaction stages, thereby enabling to reduce the activation stage passed until a steady state is reached, that is, the induction period and to sustain high activity in the steady state over a long period of time.

In the process for the preparation of organohalosilanes, the metallic silicon particles used preferably have a mean particle size in the range of 10 μm to 10 mm, more preferably 20 μm to 500 μm, and a purity of at least 97% by weight, especially at least 98% by weight.

The organohalide is represented by RX wherein R is alkyl or aryl and X is halogen. Preferably, R is methyl or phenyl, and most preferably methyl. The halogen atoms represented by X are usually Cl and Br. Illustrative examples of the organohalide include methyl chloride, ethyl chloride, propyl chloride, methyl bromide, ethyl bromide, benzene chloride and benzene bromide. Of these, methyl chloride and benzene chloride are preferable. Methyl chloride is most useful in the industry because dimethylchlorosilane produced therefrom finds a wide variety of applications as the raw material for many silicone resins.

In the formula: $R_n SiX_{4-n}$, n is 2 in large part. Preferably the organohalosilane product contains at least 80%, especially at least 85% by weight of the compound wherein n is 2.

The copper catalyst used herein may be selected from various forms of copper including elemental copper (or metallic copper) such as powdered copper and stamped copper, and copper compounds such as cuprous oxide, cupric oxide, copper halides (e.g., copper chloride) and copper acetate. An appropriate amount of the copper catalyst blended is about 0.1 to 10 parts, and more preferably about 2 to 8 parts by weight per 100 parts by weight of the metallic silicon powder.

The invention relates to the form of a co-catalyst which is used as an additive to the copper catalyst, which rapidly exerts its effects in Rochow reaction, and which comprises zinc, tin or the like. The high and rapid action of the co-catalyst originates from the strains contained in a metal copper alloy powder co-catalyst and the energy thereof. Zinc, which is generally used in the highest concentration among the co-catalysts employed in Rochow reaction together with the copper catalyst, can be uniformly mixed with copper in any mixing ratio to form an alloy which is as ductile as metallic copper. Other elements which are employed as the co-catalyst in Rochow reaction are used in lower concentrations than zinc, and copper or copper alloys containing small amounts of these elements also maintain ductility comparable to that of metallic copper and brass. These alloys having high ductility can be easily worked even at low temperature as by rolling or forging. Such working introduces a substantial amount of lattice strain in the metal structure, which is preserved unless heated. Since heating in an inert gas causes the strain to be relieved from the alloy and largely alters the physical properties thereof, this heating, generally known as annealing, is an important operation in the alloy working process. Since atoms rearrange upon relaxation of the strain energy, the physical state in which this rearrangement is taking place corresponds to a chemically highly active state.

Figure 1B:
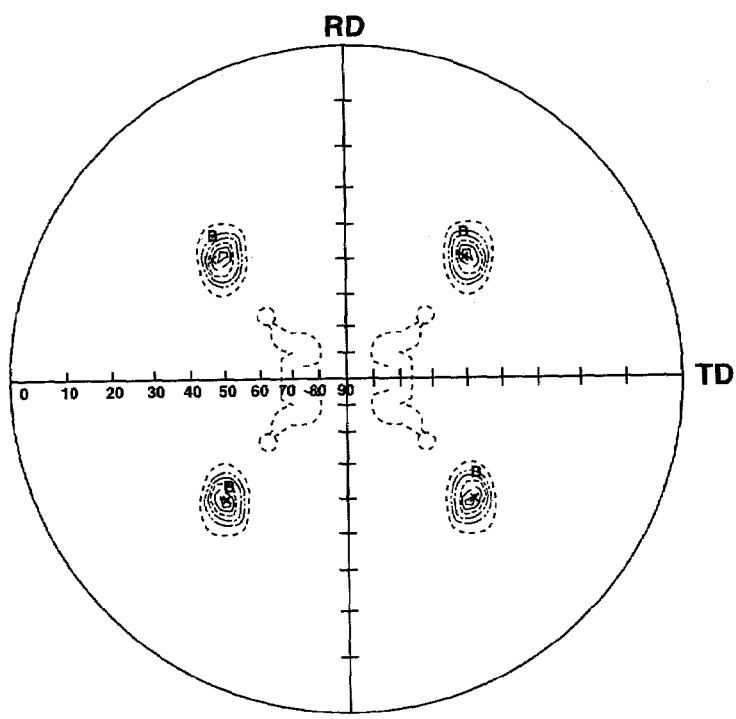

The active state following this crystallographic change is described by referring to thermal analysis data, especially the thermal analysis data of copper serving as the matrix. The result of measurement of the crystallographic change is shown in FIG. 1A, based on which the alteration following this change is described. This is the data of a pole figure obtained by analyzing crystal planes and crystal axes by means of an x-ray diffraction apparatus, from which the orientation of crystal grains is determinable. Since it is difficult to conduct diffraction analysis on the actual copper catalyst which is a powder, analysis is made on a rolled copper foil in which crystal lattices are significantly distorted. It is seen from the result that the surface of the rolled copper foil consists of (111) plane, and [200] axes are, in large part, oriented unidirectionally at an angle of about 70 degrees from that plane. This largely differs from the stable theoretical value depicted at B in the diagram. In contrast, the rolled copper foil which has been heated at 300° C. in an inert gas gives the analytic result shown in FIG. 1B in which [200] axes are oriented at an angle of about 35 degrees and at an equal spacing, with an angle of about 90 degrees between the axes. This is a stable crystal structure with orientation matching the stable theoretical value. It reveals that the heat treatment of a rolled copper foil at 300° C. in an inert gas gives rise to annealing whereby the lattice strain introduced upon rolling is relaxed.

Figure 2:
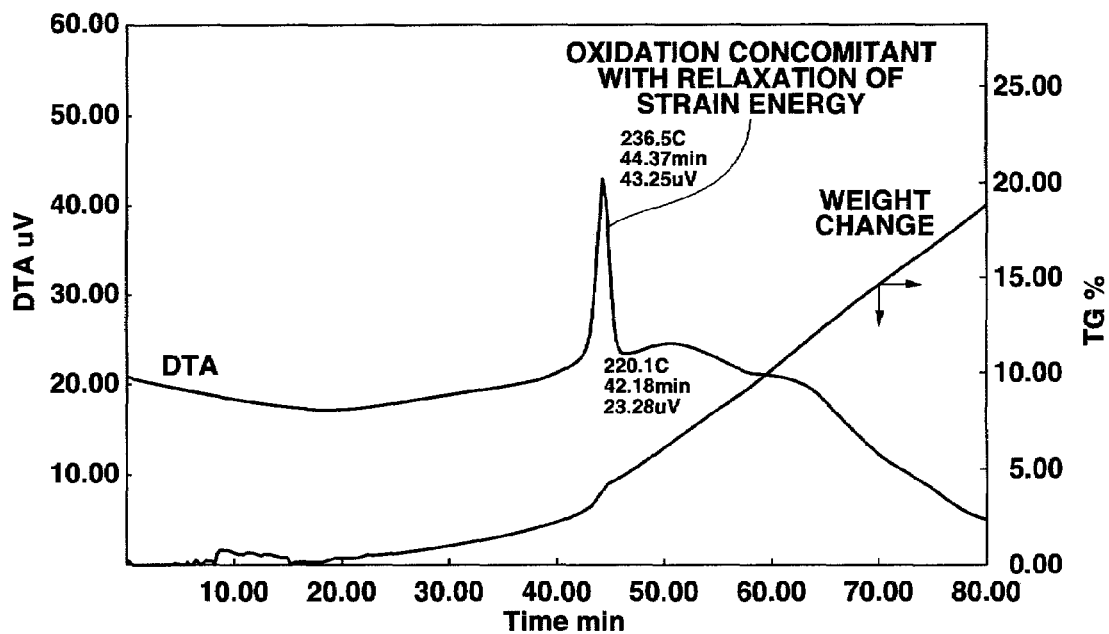
FIG. 2 is a diagram of differential thermal analysis in an air atmosphere of a strained copper powder (stamped copper).
Figure 3:
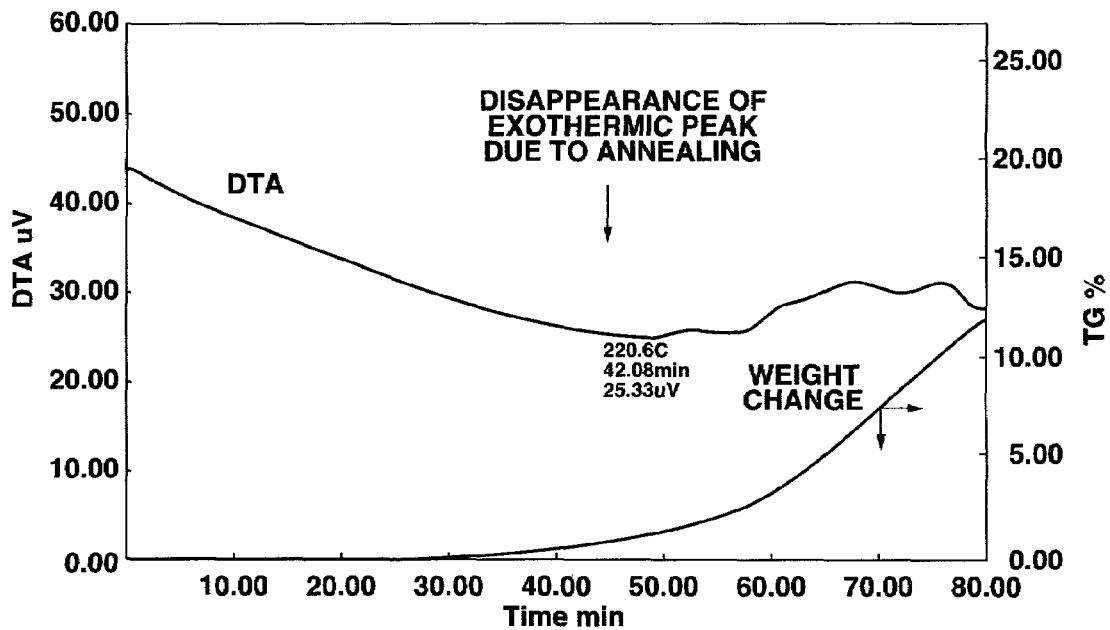
FIG. 3 is a diagram of differential thermal analysis in an air atmosphere of a copper powder obtained by annealing a strained copper powder (stamped copper) at 300° C. in nitrogen.

FIG. 2 shows the results of differential thermobalance analysis in air (at 5° C./min) on a stamped copper powder having substantial strain energy. It is observed that rapid heat generation takes place from about 220° C. and a rapid weight gain is concomitant therewith. Thereafter, a slow weight gain continues, indicating the slow progress of oxidation into the interior. FIG. 3 shows the results of the same analysis on a stamped copper powder which has been heated at 300° C. in an inert gas ($N_2$), that is, annealed, in which no such change (heat generation peak) is observed. As seen from these observations, the change indicates that the rearrangement of atoms occurs as a result of relaxation of strain energy and the surface becomes highly active at this point of time. That is, the incipient heat generation temperature and the exothermic value represent the surface activity of a metal copper catalyst.

Figure 4:
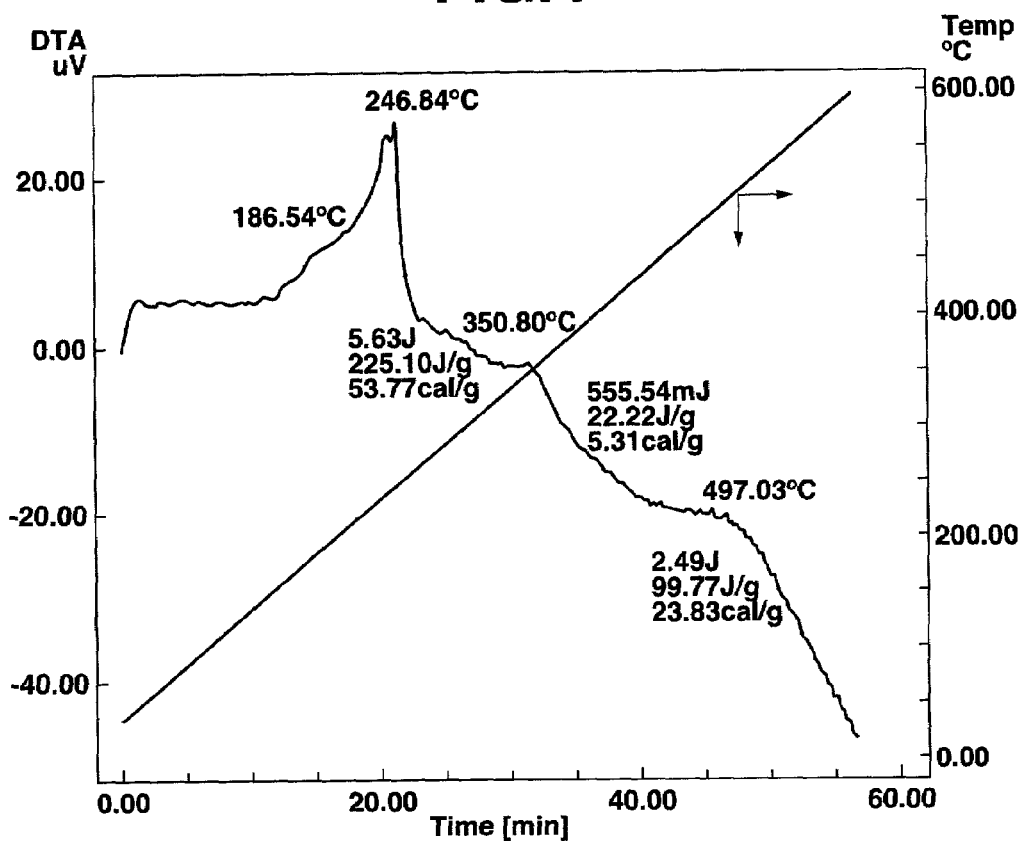
FIG. 4 is a diagram of differential thermal analysis in an air atmosphere of a strained brass powder (stamped brass powder, Cu:Zn=4:1).

FIG. 4 shows the results of differential thermal analysis (DTA) carried out on a stamped brass powder (Cu/Zn= 80/20) in air. It is seen that heat treating the stamped brass powder at 350° C. in an inert gas provides annealing, whereby the lattice strain induced upon rolling is relaxed. As seen from these observations, the change indicates that the rearrangement of atoms occurs as a result of relaxation of strain energy and the surface becomes highly active at this point of time. Stated again, the incipient heat generation temperature and the exothermic value represent the surface activity of a metal copper catalyst.

With respect to the form in a working state of the co-catalyst for Rochow reaction, it reacts in a first stage with the organic halide as the reaction gas to form a chloride, which propagates through the gas phase. Therefore, the activity is to be determined in terms of the factor that represents ease of reaction with the organic halide. From this standpoint, the activity of various co-catalysts, specifically for reaction with methyl chloride taken on the assumption of methylchlorosilane synthesis reaction, is described by referring to the results of thermal analysis. It is noted that although the addition of any co-catalyst in chloride form is advantageous on the laboratory level, the co-catalyst is preferably added in long acting form so as to be uniformly present in the system because the actual reaction is a fluidized bed reaction. Since co-catalysts other than zinc are used in relatively low concentrations, they are preferably added in admixture with other components, especially in alloy form. Then a comparison from this point of view is also involved in the following description.

Figure 5:
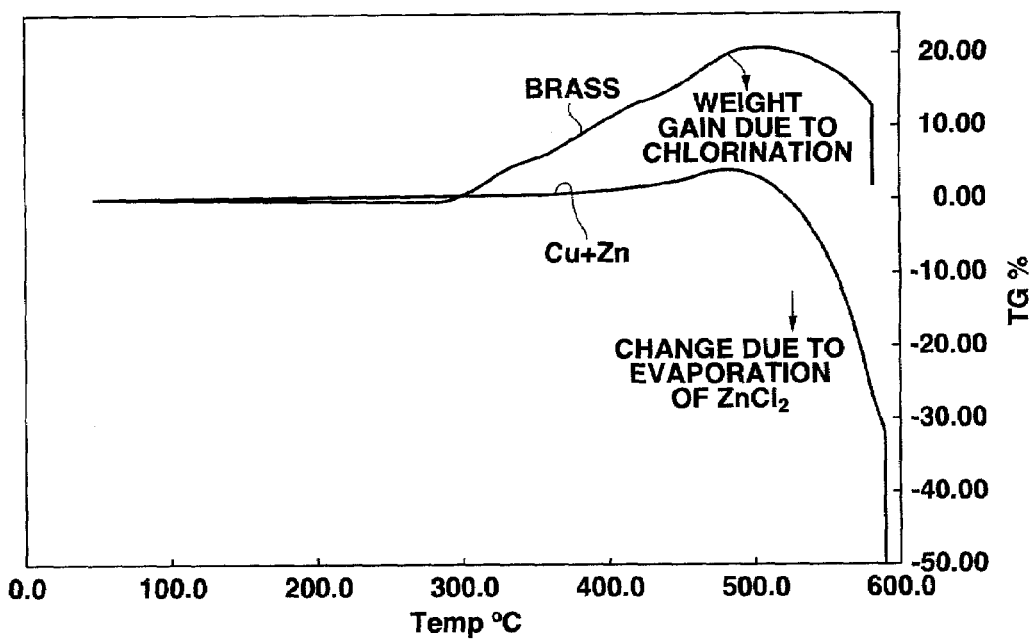
FIG. 5 is a diagram of thermobalance analysis in a methyl chloride atmosphere of a brass powder (Cu:Zn=4:1) and a mixed copper-zinc powder.

Reference is first made to zinc which is most commonly used as the co-catalyst and in relatively large addition amounts. Zinc forms a uniform ductile alloy (or brass) with copper in an arbitrary ratio. FIG. 5 shows the results of thermobalance analysis in methyl chloride of a mixed copper-zinc powder and a brass powder containing 20% of zinc (obtained by annealing stamped zinc powder by the method to be described later). As seen from these results, the brass powder, despite the lower zinc content of 20%, starts to gain weight by chlorination at a lower temperature and at a higher rate. This indicates that alloys are more susceptible to chlorination. It is noted that a weight loss at higher temperatures is due to evaporation of zinc chloride.

Figure 6:
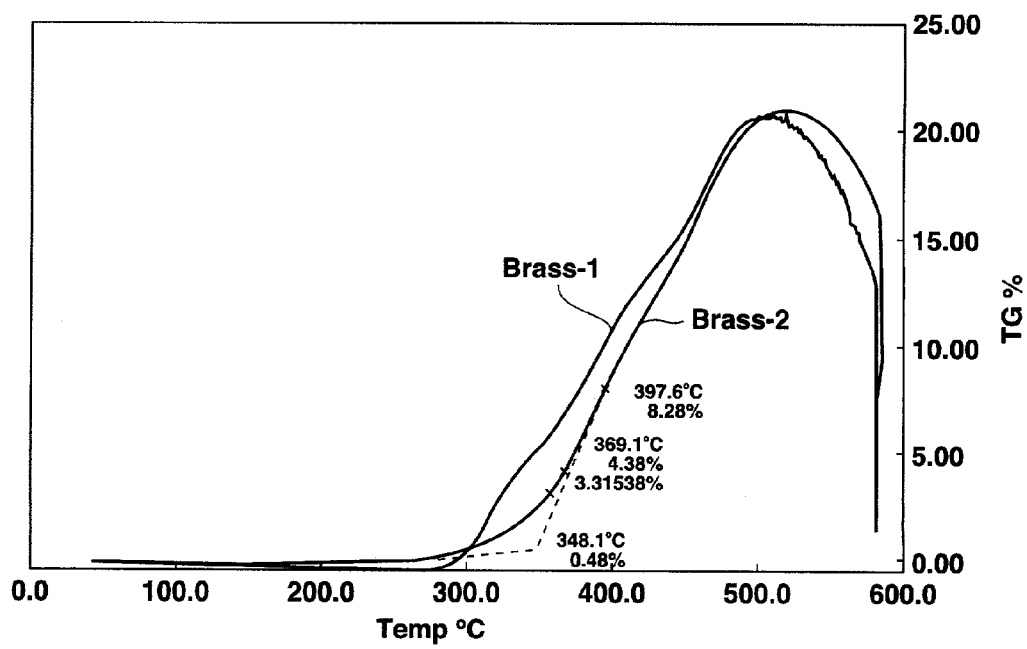
FIG. 6 is a diagram of thermobalance analysis in a methyl chloride atmosphere of a strained brass powder (stamped brass) before and after annealing at 350° C. in nitrogen.

FIG. 6 shows the results of thermobalance analysis in a methyl chloride stream of a brass powder (Brass-1) containing substantial strain energy within it, obtained by grinding a brass powder containing 20% of zinc into flakes by a stamping technique, and a brass powder (Brass-2) having the strain energy relieved to substantially nil, obtained by heating or annealing the above brass powder in an inert gas (nitrogen gas) stream at 350° C. for one hour. As seen from these results, for the non-annealed powder, the weight gain due to chlorination of zinc becomes significant from about 300° C. which is approximate to the methylsilane reaction temperature, whereas the annealed powder in which the strain energy has been relieved exhibits the same change from about 350° C. Although various physical properties including specific surface area are identical, the weight change, that is, ease of chlorination largely differs before and after annealing. This demonstrates the important role of strain energy in the relevant reaction. In Rochow reaction, immediately after an organohalide is passed to a heated charge of contact mass to start reaction, the selectivity of dihalogenosilane is very low. This is true particularly in the synthesis of methylchlorosilane, with a large amount of by-product methyltrichlorosilane being formed immediately after the onset of reaction. This phenomenon is improved.

Figure 7:
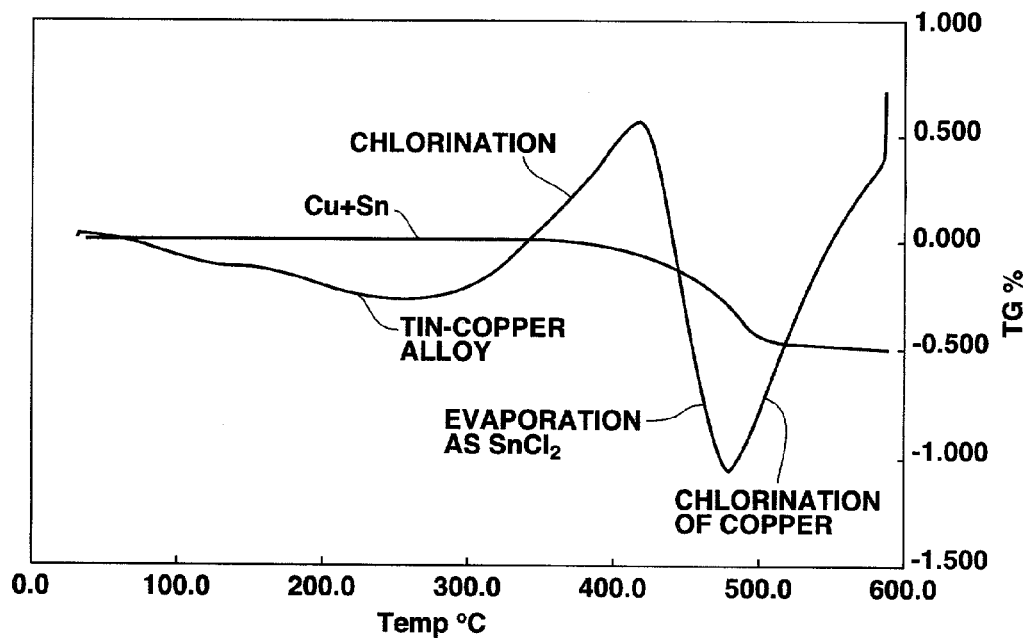
FIG. 7 is a diagram of thermobalance analysis in a methyl chloride atmosphere of a strained copper-tin alloy powder (stamped powder, tin content 5%) and a mixed copper-tin powder (for metallic tin, the scale being reduced to 1/20 of the actual measurement in order to normalize the weight).

Next reference is made to tin. FIG. 7 shows the results of thermobalance analysis in methyl chloride of an annealed alloy powder obtained by grinding an ingot of copper with 0.5% tin by a stamping technique and annealing the resulting alloy powder, and a mixed copper-tin powder. It is noted that since the tin content of tin-copper alloy is very low, the weight change of the tin powder is corrected to 1/20 of the actual measurement. A weight gain from a lower temperature is observed for the alloy powder having strain, indicating that a strained alloy is more effective. The same applies to other co-catalysts such as antimony and phosphorus.

As mentioned above, the activity of a co-catalyst in a particular form during reaction must be determined by the ease of chlorination of a co-catalyst element in a reaction gas atmosphere. It has been found from this standpoint that alloys of co-catalyst elements with copper as the catalyst, and especially those obtained by rolling, stamping or otherwise working alloys of co-catalyst elements with copper in a ductility-improving ratio so that the metal structure may have substantial strain energy of crystal lattices are more active than co-catalyst elements alone. More specifically, when a copper alloy co-catalyst having strain energy is introduced into the reaction system during Rochow reaction, the strain is relieved in the reaction environment, at which time rearrangement of copper and co-catalyst atoms takes place so that active copper alloy surfaces rapidly develop. As understood from the foregoing, the activity of the copper alloy co-catalyst can be indirectly determined in terms of the incipient heat generation temperature (i.e., the incipient oxidation temperature) and the exothermic value on differential thermal analysis (DTA) or differential scanning calorimeter (DSC) analysis in an air atmosphere or air stream as well as the BET specific surface area or air-permeability specific surface area which is the surface area of the co-catalyst itself.

Of these analyses, the differential thermal analysis (DTA) is described. DTA is to measure a thermal change of a sample by heating in a measurement atmosphere (in this case, an air atmosphere) the sample and a reference substance which is thermally stable under the measurement atmosphere (in this case, α-alumina powder) at a constant rate (e.g., 5° C./min), and measuring a difference between temperatures of the sample and the reference substance. Since the strain whose energy is greater is relieved at a lower temperature, heat generation begins at a lower temperature. For particles having a larger surface area, a higher exothermic peak is measured. The BET specific surface area is measured by way of adsorption of a gas, and the air-permeability specific surface area is measured in terms of air resistance and correlated to the ease of contact with a gas.

Based on the foregoing, the present invention uses as the co-catalyst a copper alloy with an element having co-catalytic activity such as zinc, tin, antimony, phosphorus or aluminum, containing substantial strain energy, and more illustratively, a copper alloy foil powder obtained by grinding a rolled copper alloy foil, a stamped copper alloy powder obtained by stamping a rolled copper alloy foil, electrolytic copper alloy particles, machined powder, etc. for stretching and comminution, or a microscopic copper alloy powder such as atomized copper alloy. That is, a thermally active copper alloy containing substantial strain energy therein is used as the co-catalyst. Preferably the copper alloy co-catalyst contains the crystal lattice strain energy which relaxes at a temperature of up to 400° C., and has a specific surface area of 0.05 to 2.0 $m^2/g$, more preferably 0.1 to 1.0 $m^2/g$, most preferably 0.2 to 0.8 $m^2/g$, as measured by the BET or air-permeability method. Also preferably, the copper alloy co-catalyst, when heated in air, undergoes rapid surface oxidation concomitant with the relaxation of the strain energy. On air flow differential thermal analysis (DTA), the co-catalyst preferably exhibits an incipient heat generation temperature of up to 400° C., more preferably 150 to 400° C., most preferably 200 to 400° C., with an exothermic value of 1 to 80 cal/g, more preferably 10 to 80 cal/g, most preferably 30 to 70 cal/g.

For the copper alloy to be used as the co-catalyst, the element having co-catalytic activity to be alloyed with copper is selected from zinc, tin, antimony, phosphorus, aluminum, etc. and mixtures thereof. The copper alloy used herein is a copper base alloy, specifically having a copper content of 50 to 99.9%, especially 70 to 99% by weight.

In the organohalosilane synthesis, the amount of the co-catalyst used is a sufficient amount to allow the element having co-catalytic activity to exert its co-catalytic effect. The amount of the co-catalyst, though varies with the type of co-catalytic element, is usually in the range of about 10 to 10,000 ppm, especially about 20 to 3,000 ppm of the co-catalytic element based on the weight of metallic silicon.

The process of the invention can be carried out in any of fixed bed reactors, stirred bed reactors and fluidized bed reactors. From the industrial aspect, a fluidized bed reactor suited for continuous operation is employed. Reaction is effected at a temperature of about 200 to 600° C., preferably about 250 to 400° C., and more preferably about 250 to 350° C.

In the step of heating the contact mass or imparting catalytic activity to the contact mass, an inert gas is used for fluidizing the contact mass in the reactor. Such an inert gas may be nitrogen, helium or argon gas, for example, with the nitrogen gas being preferable from the economic standpoint. The flow velocity of the inert gas fed in this and subsequent steps is at least the incipient fluidization velocity of the contact mass, and preferably about 5 times the incipient fluidization velocity. A flow velocity below the range of the inert gas may make it difficult to achieve uniform fluidization of the contact mass. If the flow velocity of the inert gas is above the range, metallic silicon powder may be excessively scattered with increased losses of the inert gas and heat. It is recommended to recycle the inert gas and the organohalide.

After the contact mass is given catalytic activity as mentioned above, the organohalide is introduced into the reactor where gas-solid catalytic reaction takes place between the organohalide and metallic silicon to form organohalosilanes. The organohalide is previously heated and gasified before it is admitted into the reactor. The organohalide gas may be fed alone or combined with an inert gas in a sufficient amount to fluidize the contact mass, the fluidizing amount being determined as appropriate from the diameter of the reactor and the superficial velocity.

Figure 8:
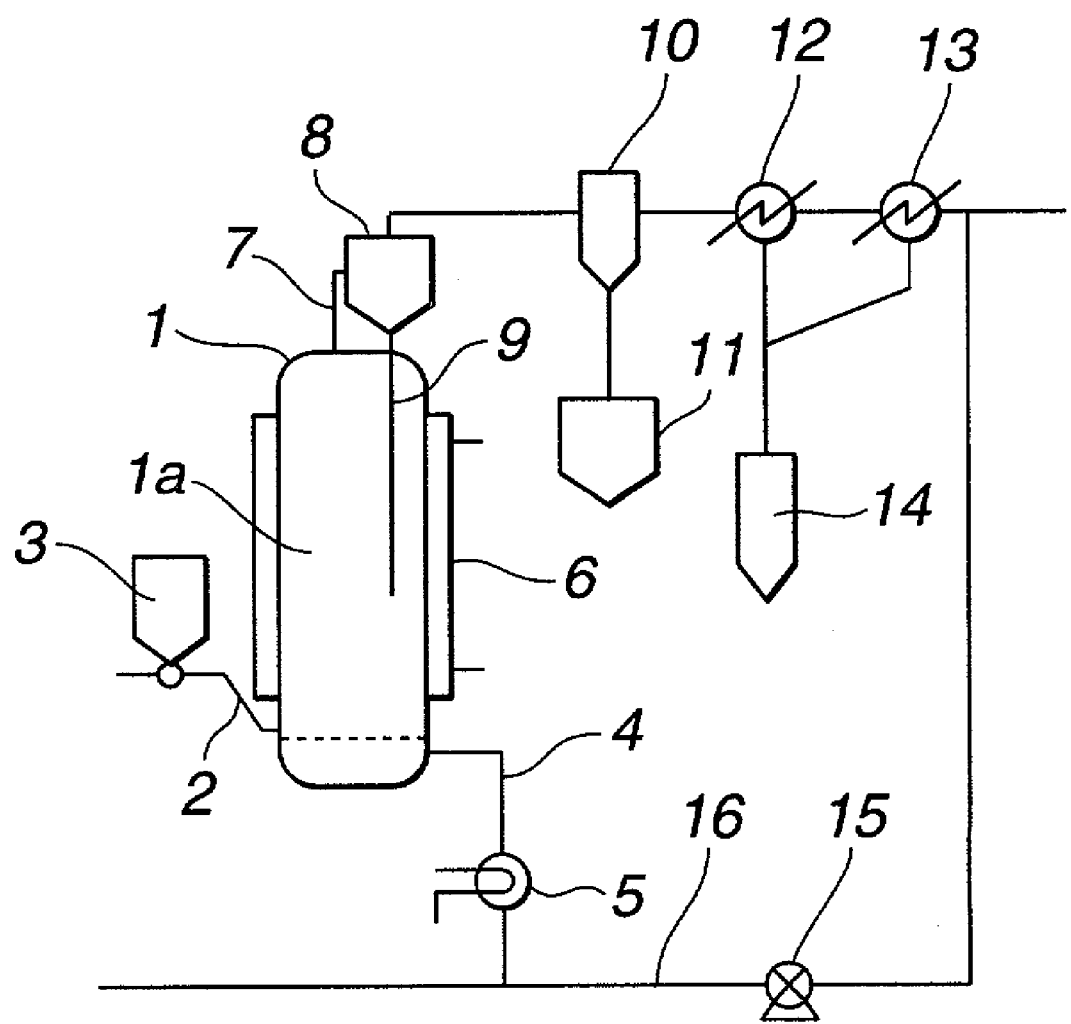
FIG. 8 is an explanation view showing one example of an organohalosilane preparing apparatus.

No particular limitation is imposed on the organohalosilane production apparatus. For example, use may be made of the apparatus shown in FIG. 8. Referring to FIG. 8, a fluidized bed reactor 1 is connected at the bottom thereof to a starting material hopper 3 via a starting material feed line 2. The metallic silicon, the copper catalyst or a catalyst mixture of the copper catalyst with the co-catalyst, and an optional promoter are introduced to the bottom of the reactor 1 from the hopper 3 via the feed line 2. An organohalide feed line 4 equipped with a heater 5 is also connected to the bottom of the reactor 1 for introducing the organohalide in gas or vapor form into the reactor 1 at its bottom. A fluidized bed 1a of the metallic silicon and catalyst is then formed within the reactor 1. The apparatus is also equipped with a cooler 6.

The organohalide gas or vapor is preferably introduced at a linear flow rate of 2 to 10 cm/s under steady-state conditions. The reaction is carried out at 250 to 400° C., and preferably 250 to 350° C.

The organohalosilane formed in the reaction passes through a discharge line 7 connected to the top of the reactor 1, and is introduced into a first cyclone 8, where entrained solid particles are separated off. The solid particles are returned to the fluidized bed 1a via a solid particle return line 9. The organohalosilane then passes to a second cyclone 10, where more entrained solid particles are separated off and stored in a particle storage tank 11. Next, the organohalosilane is condensed in a first silane condenser 12, then in a second silane condenser 13, and is collected and stored in a silane storage tank 14. Some or all of the waste gases remaining after the solid particles have been separated off and the organohalosilane has been condensed and removed is returned once again to the reactor 1 through an organohalide return line 16 equipped with a circulating gas-type compressor 15. The return line 16 is connected to the organohalide feed line 4.

EXAMPLE

Examples of the invention are given below by way of illustration and not by way of limitation. Parts are by weight.

Example 1

An 8 cm diameter steel reactor equipped with a spiral stirrer like that shown in FIG. 8 was charged with 100 parts of a metallic silicon powder (aluminum content 0.17% by weight) having a mean particle size of 50 $\mu$m. A nitrogen gas was introduced into the reactor at a linear flow rate of 2 cm/sec to fluidize the reactor contents while stirring with the spiral stirrer, and the temperature was raised to 280° C. Then, 3 parts of a copper catalyst prepared by stamping and having an air-permeability specific surface area of 0.80 $m^2$/g, a DTA incipient heat generation temperature of 219° C., and an exothermic value at the exothermic peak of 26.3 cal/g and 1 part of a brass powder (zinc concentration 20%) prepared by stamping and having an air-permeability specific surface area of 0.15 $m^2$/g, a DTA incipient heat generation temperature of 170° C., and an exothermic value at the exothermic peak of 25.9 cal/g were added to the reactor. Methyl chloride was slowly added to effect reaction while controlling the reaction temperature to 280 to 330° C., and ultimately fed at a linear flow rate of 7 cm/sec for the reaction to proceed. The reaction was continued for 6 hours, at which point it was brought to completion. Table 1 shows the average rate of silane formation, the consumption of metallic silicon, and the composition of the silane formed, at both 1 hour and 6 hours after the start of reaction.

Example 2

After the reactor charged with 100 parts of a metallic silicon powder (aluminum content 0.14% by weight) having a mean particle size of 50 $\mu$m was heated at 280° C. in a nitrogen gas stream as in Example 1, 3 parts of a copper catalyst prepared by stamping and having an air-permeability specific surface area of 0.80 $m^2$/g, a DTA incipient heat generation temperature of 219° C., and an exothermic value at the exothermic peak of 26.3 cal/g, 1 part of a brass powder (zinc concentration 20%) prepared by stamping and having an air-permeability specific surface area of 0.15 $m^2$/g, a DTA incipient heat generation temperature of 170° C., and an exothermic value at the exothermic peak of 25.9 cal/g, and 0.1 part of a stamped copper-tin alloy powder (containing 0.5% tin) were added to the reactor. Methyl chloride was slowly added to effect reaction while controlling the reaction temperature to 280 to 330° C., and ultimately fed at a linear flow rate of 7 cm/sec for the reaction to proceed. The reaction was continued for 6 hours, at which point it was brought to completion. Table 1 shows the average rate of silane formation, the consumption of metallic silicon, and the composition of the silane formed, at both 1 hour and 6 hours after the start of reaction.

Example 3

After the reactor charged with 100 parts of a metallic silicon powder (aluminum content 0.14% by weight) having a mean particle size of 50 $\mu$m was heated at 280° C. in a nitrogen gas stream as in Example 1, 3 parts of a copper catalyst prepared by stamping and having an air-permeability specific surface area of 0.80 $m^2$/g, a DTA incipient heat generation temperature of 219° C., and an exothermic value at the exothermic peak of 26.3 cal/g, 1 part of a brass powder (zinc concentration 20%) prepared by stamping and having an air-permeability specific surface area of 0.15 $m^2$/g, a DTA incipient heat generation temperature of 170° C., and an exothermic value at the exothermic peak of 25.9 cal/g, and 0.1 part of a stamped copper-antimony alloy powder (containing 0.5% antimony) were added to the reactor. Methyl chloride was slowly added to effect reaction while controlling the reaction temperature to 280 to 330° C., and ultimately fed at a linear flow rate of 7 cm/sec for the reaction to proceed. The reaction was continued for 6 hours, at which point it was brought to completion. Table 1 shows the average rate of silane formation, the consumption of metallic silicon, and the composition of the silane formed, at both 1 hour and 6 hours after the start of reaction.

Comparative Example 1

After the reactor charged with 100 parts of a metallic silicon powder (aluminum content 0.17% by weight) having a mean particle size of 50 $\mu$m was heated at 280° C. in a nitrogen gas stream as in Example 1, a mixture of 3 parts of a copper catalyst prepared by stamping and having an air-permeability specific surface area of 0.80 $m^2$/g, a DTA incipient heat generation temperature of 218° C., and an exothermic value at the exothermic peak of 24.9 cal/g and 1 part of a brass powder obtained from a stamped brass powder (zinc concentration 20%) having an air-permeability specific surface area of 0.15 $m^2$/g, a DTA incipient heat generation temperature of 170° C., and an exothermic value at the exothermic peak of 25.9 cal/g, by annealing it in nitrogen gas at 350° C. for one hour so that the DTA exothermic peak disappeared, the annealed powder having an air-permeability specific surface area of 0.14 $m^2$/g, was added to the reactor. Methyl chloride was slowly added to effect reaction while controlling the reaction temperature to 280 to 330° C., and ultimately fed at a linear flow rate of 7 cm/sec for the reaction to proceed. The reaction was continued for 6 hours, at which point it was brought to completion. Table 1 shows the average rate of silane formation, the consumption of metallic silicon, and the composition of the silane formed, at both 1 hour and 6 hours after the start of reaction.

TABLE 1

| | Example 1 | Example 2 | Example 3 | Comparative Example 1 |
|---|---|---|---|---|
| Metallic Si powder | Al 0.18% | Al 0.14% | Al 0.14% | Al 0.18% |
| Copper catalyst: | | | | |
| flake metallic Cu, 3 parts | flake | flake | flake | flake |
| Air-permeability specific surface area ($m^2/g$) | 0.80 | 0.80 | 0.80 | 0.80 |
| DTA incipient heat generation temperature (°C.) | 218 | 218 | 218 | 218 |
| Co-catalyst 1: | | | | |
| brass powder (Zn 20%), 1 part | flake | flake | flake | annealed |
| Air-permeability specific surface area ($m^2/g$) | 0.15 | 0.15 | 0.15 | 0.14 |
| DTA incipient heat generation temperature (°C.) | 173 | 173 | 173 | — |
| Co-catalyst 2: | | | | |
| (Cu—Sn, Sn 0.5%), 0.1 part | — | flake | — | — |
| (Cu—Sb, Sb 0.5%), 0.1 part | — | — | flake | — |
| Initial (1 hr) | | | | |
| Average rate of silane formation* | 15.5 | 16.5 | 14.5 | 16.0 |
| $Me_2SiCl_2$ (%) | 78 | 80 | 77 | 70 |
| $MeSiCl_3$/$Me_2SiCl_2$ ratio | 0.10 | 0.095 | 0.10 | 0.20 |
| Accumulation (6 hr) | | | | |
| Average rate of silane formation* | 18.5 | 17.3 | 16.3 | 19.8 |
| $Me_2SiCl_2$ (%) | 87 | 88 | 85 | 81 |
| $MeSiCl_3$/$Me_2SiCl_2$ ratio | 0.075 | 0.070 | 0.075 | 0.10 |

*g-silane/100 g · hr

The co-catalyst according to the invention, when used in Rochow reaction for organohalosilane synthesis, can reduce the activation time taken until a steady state is reached, which has been an outstanding problem in Rochow reaction, maintain the steady state over time and increase the selectivity of desired diorganodihalosilane for eventually increasing the yield based on the starting silicon. Since the co-catalyst plays an important role in Rochow reaction, the prior art approach involves a by-pass process of carrying out empirical reaction with a co-catalyst for evaluating its activity, prior to using it in industrial reaction. The present invention overcomes this by-pass process problem.

Japanese Patent Application No. 2001-110805 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing organohalosilanes, comprising the step of reacting metallic silicon particles with an organohalide in the presence of a copper catalyst and a co-catalyst comprising a copper alloy powder which is an alloy of copper with at least one element selected from the group consisting of zinc, tin, antimony, phosphorus and aluminum and containing substantial strain energy so that the alloy, on air flow differential thermal analysis, exhibits an incipient heat generation temperature of up to 400° C. with an exothermic value of 1 to 80 cal/g
    wherein the alloy having substantial strain energy is obtained by a mechanical working of rolling or stamping
    wherein the co-catalyst has a specific surface area of 0.1 to 2.0 $m^2/g$ as measured by the BET or air-permeability method.

2. The process of claim 1, wherein the copper alloy powder is a copper alloy foil powder, stamped copper alloy powder or microscopic copper alloy powder.

3. A process for preparing organosilanes, comprising the step of reacting metallic silicon particles with an organohalide in the presence of a copper catalyst and a co-catalyst comprising a copper alloy powder which is an alloy of copper with at least one element selected from the group consisting of zinc, tin, antimony, phosphorous and aluminum and containing substantial strain energy so that the alloy, on air flow differential thermal analysis, exhibits an incipient heat generation temperature of up to 400° C. with an exothermic value of 1 to 80 cal/g, wherein the alloy having substantial strain energy is obtained by a mechanical working of rolling or stamping and wherein the co-catalyst possesses the crystal lattice strain energy which relaxes at a temperature of up to 400° C., and has a specific surface area of 0.05 to 2.0 $m^2/g$ as measured by the BET or air-permeability method.

4. The process of claim 1, wherein the co-catalyst when heated in air, undergoes rapid surface oxidation concomitant with the relaxation of the strain energy.

5. The process of claim 1, wherein the alloy, on air flow differential thermal analysis, exhibits an incipient heat generation temperature of 150 to 400° C.

6. The process of claim 1, wherein the organohalosilane is diorganodichlorosilane.

* * * * *